US011042807B2

(12) United States Patent
Kapur et al.

(10) Patent No.: US 11,042,807 B2
(45) Date of Patent: Jun. 22, 2021

(54) SYSTEMS AND METHODS FOR PROCESSING IMAGES TO CLASSIFY THE PROCESSED IMAGES FOR DIGITAL PATHOLOGY

(71) Applicant: PAIGE.AI, Inc., New York, NY (US)

(72) Inventors: Supriya Kapur, New York, NY (US); Christopher Kanan, Rochester, NY (US); Thomas Fuchs, New York, NY (US); Leo Grady, Darien, CT (US)

(73) Assignee: PAIGE.AI, Inc., New York, NY (US)

( * ) Notice: Subject to any disclaimer, the term of this patent is extended or adjusted under 35 U.S.C. 154(b) by 0 days.

(21) Appl. No.: 17/112,435

(22) Filed: Dec. 4, 2020

(65) Prior Publication Data

US 2021/0117826 A1    Apr. 22, 2021

Related U.S. Application Data

(63) Continuation of application No. 16/875,616, filed on May 15, 2020, now Pat. No. 10,891,550.

(Continued)

(51) Int. Cl.
*G06N 5/04* (2006.01)
*G06N 20/00* (2019.01)
*G06T 7/00* (2017.01)

(52) U.S. Cl.
CPC .............. *G06N 5/04* (2013.01); *G06N 20/00* (2019.01); *G06T 7/0012* (2013.01);
(Continued)

(58) Field of Classification Search
CPC ........ G06N 5/04; G06N 20/00; G06T 7/0012; G06T 2207/20081; G06T 2207/20076; G06T 2207/30168
See application file for complete search history.

(56) References Cited

U.S. PATENT DOCUMENTS 7,761,240 B2 *  7/2010  Saidi ..................... G06T 7/0012
                                                                 702/19
8,280,132 B2 * 10/2012  Madabhushi ............. G06T 7/11
                                                                 382/128
(Continued)

FOREIGN PATENT DOCUMENTS

WO       2014153423 A2    9/2014
WO       2018156133 A1    8/2018

OTHER PUBLICATIONS

Daisuke Komura, Shumpei Ishikawa., "Machine Learning Methods for Histopathological Image Analysis," Computational and Structural Biotechnology Journal. 2018.

(Continued)

*Primary Examiner* — Kim Y Vu
*Assistant Examiner* — Molly Delaney
(74) *Attorney, Agent, or Firm* — Bookoff McAndrews, PLLC

(57) ABSTRACT

Systems and methods are disclosed for receiving a target image corresponding to a target specimen, the target specimen comprising a tissue sample of a patient, applying a machine learning model, which may also be known as a machine learning system, to the target image to determine at least one characteristic of the target specimen and/or at least one characteristic of the target image, the machine learning model having been generated by processing a plurality of training images to predict at least one characteristic, the training images comprising images of human tissue and/or images that are algorithmically generated, and outputting the at least one characteristic of the target specimen and/or the at least one characteristic of the target image.

20 Claims, 10 Drawing Sheets

Related U.S. Application Data

(60) Provisional application No. 62/848,703, filed on May 16, 2019.

(52) U.S. Cl.
CPC ............... *G06T 2207/20076* (2013.01); *G06T 2207/20081* (2013.01); *G06T 2207/30168* (2013.01)

(56) References Cited

U.S. PATENT DOCUMENTS

| | | | | |
|---|---|---|---|---|
| 9,959,615 | B2* | 5/2018 | Liang | G06K 9/4628 |
| 10,109,052 | B2* | 10/2018 | Chefd'hotel | G06T 7/0012 |
| 10,650,929 | B1* | 5/2020 | Beck | G16H 50/70 |
| 2005/0165290 | A1* | 7/2005 | Kotsianti | G06T 7/0012 |
| | | | | 600/407 |
| 2014/0247972 | A1* | 9/2014 | Wang | G06K 9/0014 |
| | | | | 382/133 |
| 2016/0232425 | A1* | 8/2016 | Huang | G06T 7/0012 |
| 2017/0329894 | A1* | 11/2017 | Kennedy | G16B 40/20 |
| 2018/0053296 | A1* | 2/2018 | Hattori | G01N 33/4833 |
| 2018/0211380 | A1* | 7/2018 | Tandon | G06K 9/6271 |
| 2018/0247107 | A1* | 8/2018 | Murthy | G06K 9/4628 |
| 2018/0253590 | A1* | 9/2018 | Lloyd | G01N 33/4833 |
| 2019/0080450 | A1* | 3/2019 | Arar | G06T 7/0012 |
| 2019/0188850 | A1* | 6/2019 | Reicher | A61B 6/03 |
| 2019/0206056 | A1* | 7/2019 | Georgescu | G06K 9/00523 |
| 2019/0228527 | A1* | 7/2019 | Ramirez | G06T 7/41 |
| 2020/0069973 | A1* | 3/2020 | Lou | A61B 6/5211 |
| 2020/0129263 | A1* | 4/2020 | Izadyyazdanabadi | G06K 9/00134 |
| 2020/0160032 | A1* | 5/2020 | Allen | G06N 3/0454 |

OTHER PUBLICATIONS

International Search Report and Written Opinion issued in International Application PCT/US2020/033161, dated Jul. 21, 2020.

* cited by examiner

```
                    ┌──────────────────────────────────────────┐
                    │ RECEIVING A TARGET IMAGE CORRESPONDING    │
              202 ──│ TO A TARGET SPECIMEN, THE TARGET SPECIMEN │
                    │ COMPRISING A TISSUE SAMPLE OF A PATIENT   │
                    └──────────────────────┬───────────────────┘
                                           │
                                           ▼
   ┌─────────────────────────────────────────────────────────────────────┐
   │ APPLYING A MACHINE LEARNING MODEL TO THE TARGET IMAGE TO DETERMINE   │
   │ AT LEAST ONE CHARACTERISTIC OF THE TARGET SPECIMEN AND/OR AT LEAST   │
   │ ONE CHARACTERISTIC OF THE TARGET IMAGE, THE MACHINE LEARNING MODEL   │
204│ HAVING BEEN GENERATED BY PROCESSING A PLURALITY OF TRAINING IMAGES   │
   │ TO PREDICT AT LEAST ONE CHARACTERISTIC, THE TRAINING IMAGES          │
   │ COMPRISING IMAGES OF HUMAN TISSUE AND/OR IMAGES THAT ARE             │
   │ ALGORITHMICALLY GENERATED                                            │
   └───────────────────────────────┬─────────────────────────────────────┘
                                   │
                                   ▼
                    ┌──────────────────────────────────────────┐
                    │ OUTPUTTING THE AT LEAST ONE CHARACTERISTIC│
              206 ──│ OF THE TARGET SPECIMEN AND/OR THE AT LEAST│
                    │ ONE CHARACTERISTIC OF THE TARGET IMAGE   │
                    └──────────────────────────────────────────┘
                                        200
```

*FIG. 2A*

SYSTEMS AND METHODS FOR PROCESSING IMAGES TO CLASSIFY THE PROCESSED IMAGES FOR DIGITAL PATHOLOGY

RELATED APPLICATION(S)

This application is a continuation of and claims the benefit of U.S. application Ser. No. 16/875,616, filed May 15, 2020, which claims priority to U.S. Provisional Application No. 62/848,703, filed May 16, 2019, each of which are incorporated herein by reference in their entireties.

FIELD OF THE DISCLOSURE

Various embodiments of the present disclosure relate generally to image-based specimen classification and related image processing methods. More specifically, particular embodiments of the present disclosure relate to systems and methods for identifying or verifying specimen type or specimen properties based on processing images of tissue specimens.

BACKGROUND

In order to use digital pathology images within a hospital or in research environments, it can be important to categorize the specimen's tissue type, the nature of the specimen's acquisition (e.g., prostate needle biopsy, breast biopsy, breast resection, etc.), and other relevant properties of the specimen or the image. In hospital settings, tissue type information may be stored in a laboratory information system (LIS). However, the correct tissue classification information is not always paired with the image content. For example, a third party may be given anonymized access to the image content without the corresponding specimen type label stored in the LIS. Access to LIS content may be limited due to its sensitive content. Additionally, even if an LIS is used to access the specimen type for a digital pathology image, this label may be incorrect due to the fact that many components of an LIS may be manually inputted, leaving a large margin for error.

A desire exists for a way to provide solutions for incorrect or missing specimen type labels for digital pathology images, without necessarily accessing an LIS or related information database. The following disclosure is directed to systems and methods for addressing this need for classifying tissue specimens from digital pathology images.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for identifying or verifying specimen type or specimen properties from image analysis of tissue specimens.

A method for analyzing an image corresponding to a specimen includes: receiving a target image corresponding to a target specimen, the target specimen comprising a tissue sample of a patient; applying a machine learning model to the target image to determine at least one characteristic of the target specimen and/or at least one characteristic of the target image, the machine learning model having been generated by processing a plurality of training images to predict at least one characteristic, the training images comprising images of human tissue and/or images that are algorithmically generated; and outputting the at least one characteristic of the target specimen and/or the at least one characteristic of the target image.

A system for analyzing an image corresponding to a specimen includes a memory storing instructions; and a processor executing the instructions to perform a process including receiving a target image corresponding to a target specimen, the target specimen comprising a tissue sample of a patient; applying a machine learning model to the target image to determine at least one characteristic of the target specimen and/or at least one characteristic of the target image, the machine learning model having been generated by processing a plurality of training images to predict at least one characteristic, the training images comprising images of human tissue and/or images that are algorithmically generated; and outputting the at least one characteristic of the target specimen and/or the at least one characteristic of the target image.

A non-transitory computer-readable medium storing instructions that, when executed by processor, cause the processor to perform a method for analyzing an image corresponding to a specimen, the method includes receiving a target image corresponding to a target specimen, the target specimen comprising a tissue sample of a patient; applying a machine learning model to the target image to determine at least one characteristic of the target specimen and/or at least one characteristic of the target image, the machine learning model having been generated by processing a plurality of training images to predict at least one characteristic, the training images comprising images of human tissue and/or images that are algorithmically generated; and outputting the at least one characteristic of the target specimen and/or the at least one characteristic of the target image.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 2A and 2B are flowcharts illustrating exemplary methods for determining specimen property or image property information pertaining to digital pathology image(s), and using machine learning to classify a specimen, according to one or more exemplary embodiments of the present disclosure.

DESCRIPTION OF THE EMBODIMENTS

Figure 1A:
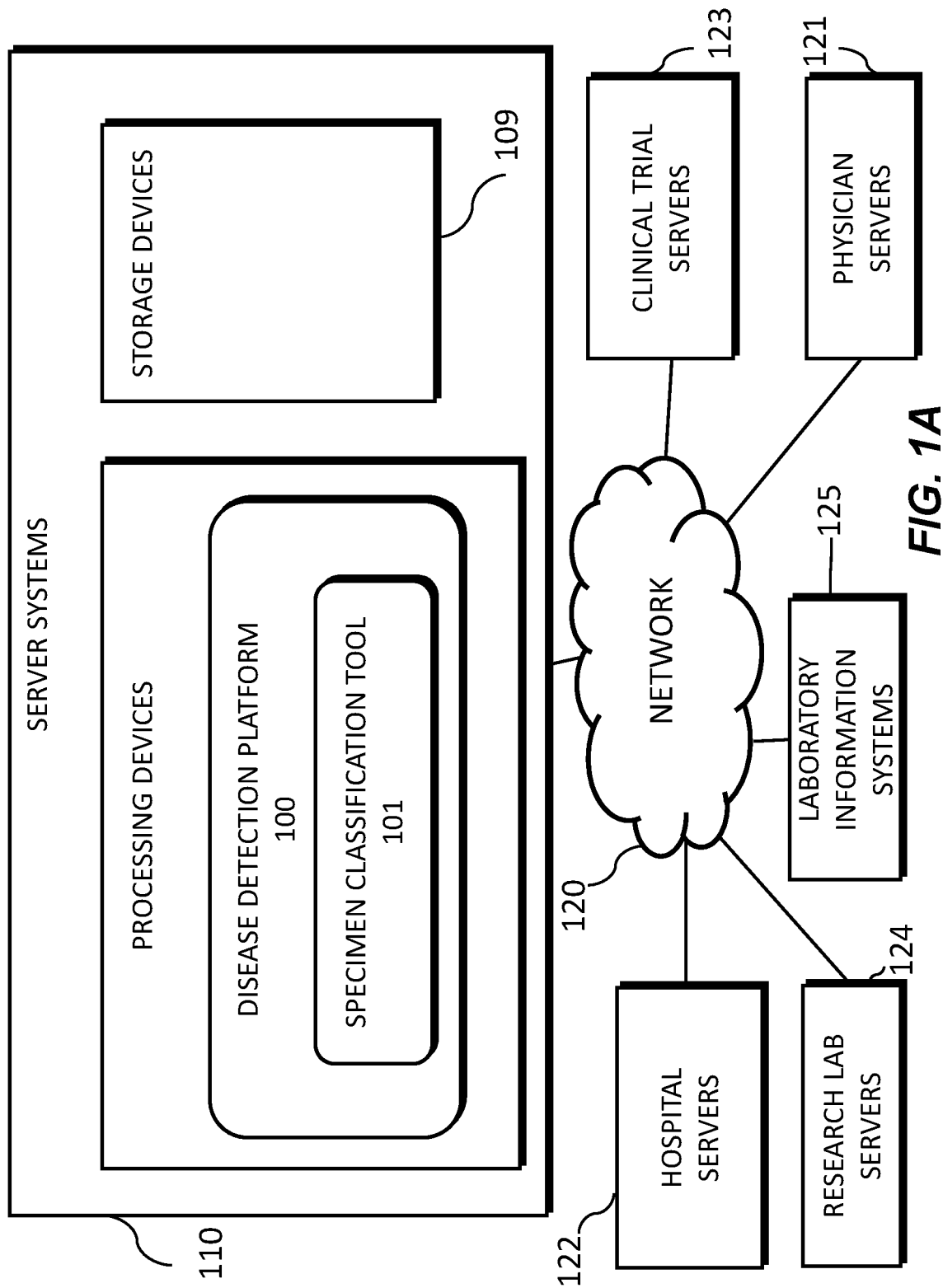
FIG. 1A illustrates an exemplary block diagram of a system and network for determining specimen property or image property information pertaining to digital pathology image(s), according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis. When uncertain of a diagnostic finding on a slide, a pathologist may order additional cut levels, stains, or other tests to gather more information from the tissue. Technician(s) may then create new slide(s) which may contain the additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in isolation. The present disclosure presents a consolidated workflow for improving diagnosis of cancer and other diseases. The workflow may integrate, for example, slide evaluation, tasks, image analysis and cancer detection artificial intelligence (AI), annotations, consultations, and recommendations in one workstation. In particular, the present disclosure describes various exemplary user interfaces available in the workflow, as well as AI tools that may be integrated into the workflow to expedite and improve a pathologist's work.

For example, computers may be used to analyze an image of a tissue sample to quickly identify whether additional information may be needed about a particular tissue sample, and/or to highlight to a pathologist an area in which he or she should look more closely. Thus, the process of obtaining additional stained slides and tests may be done automatically before being reviewed by a pathologist. When paired with automatic slide segmenting and staining machines, this may provide a fully automated slide preparation pipeline. This automation has, at least, the benefits of (1) minimizing an amount of time wasted by a pathologist determining a slide to be insufficient to make a diagnosis, (2) minimizing the (average total) time from specimen acquisition to diagnosis by avoiding the additional time between when additional tests are ordered and when they are produced, (3) reducing the amount of time per recut and the amount of material wasted by allowing recuts to be done while tissue blocks (e.g., pathology specimens) are in a cutting desk, (4) reducing the amount of tissue material wasted/discarded during slide preparation, (5) reducing the cost of slide preparation by partially or fully automating the procedure, (6) allowing automatic customized cutting and staining of slides that would result in more representative/informative slides from samples, (7) allowing higher volumes of slides to be generated per tissue block, contributing to more informed/precise diagnoses by reducing the overhead of requesting additional testing for a pathologist, and/or (8) identifying or verifying correct properties (e.g., pertaining to a specimen type) of a digital pathology image, etc.

The process of using computers to assist pathologists is known as computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (e.g., benign) or abnormal (e.g., malignant). To assist pathologists in identifying and classifying nuclei, histological stains may be used to make cells visible. Many dye-based staining systems have been developed, including periodic acid-Schiff reaction, Masson's trichrome, nissl and methylene blue, and Haemotoxylin and Eosin (H&E). For medical diagnosis, H&E is a widely used dye-based method, with hematoxylin staining cell nuclei blue, eosin staining cytoplasm and extracellular matrix pink, and other tissue regions taking on variations of these colors. In many cases, however, H&E-stained histologic preparations do not provide sufficient information for a pathologist to visually identify biomarkers that can aid diagnosis or guide treatment. In this situation, techniques such as immunohistochemistry (IHC), immunofluorescence, in situ hybridization (ISH), or fluorescence in situ hybridization (FISH), may be used. IHC and immunofluorescence involve, for example, using antibodies that bind to specific antigens in tissues enabling the visual detection of cells expressing specific proteins of interest, which can reveal biomarkers that are not reliably identifiable to trained pathologists based on the analysis of H&E stained slides. ISH and FISH may be employed to assess the number of copies of genes or the abundance of specific RNA molecules, depending on the type of probes employed (e.g. DNA probes for gene copy number and RNA probes for the assessment of RNA expression). If these methods also fail to provide sufficient information to detect some biomarkers, genetic testing of the tissue may be used to confirm if a biomarker is present (e.g., overexpression of a specific protein or gene product in a tumor, amplification of a given gene in a cancer).

A digitized image may be prepared to show a stained microscope slide, which may allow a pathologist to manually view the image on a slide and estimate a number of stained abnormal cells in the image. However, this process may be time consuming and may lead to errors in identifying abnormalities because some abnormalities are difficult to detect. Computational processes and devices may be used to assist pathologists in detecting abnormalities that may otherwise be difficult to detect. For example, AI may be used to predict biomarkers (such as the over-expression of a protein and/or gene product, amplification, or mutations of specific genes) from salient regions within digital images of tissues stained using H&E and other dye-based methods. The images of the tissues could be whole slide images (WSI), images of tissue cores within microarrays or selected areas of interest within a tissue section. Using staining methods like H&E, these biomarkers may be difficult for humans to visually detect or quantify without the aid of additional testing. Using AI to infer these biomarkers from digital images of tissues has the potential to improve patient care, while also being faster and less expensive.

The detected biomarkers or the image alone could then be used to recommend specific cancer drugs or drug combination therapies to be used to treat a patient, and the AI could identify which drugs or drug combinations are unlikely to be successful by correlating the detected biomarkers with a database of treatment options. This can be used to facilitate the automatic recommendation of immunotherapy drugs to target a patient's specific cancer. Further, this could be used for enabling personalized cancer treatment for specific subsets of patients and/or rarer cancer types.

In the field of pathology today, it may be difficult to provide systematic quality control ("QC"), with respect to pathology specimen preparation, and quality assurance ("QA") with respect to the quality of diagnoses, throughout the histopathology workflow. Systematic quality assurance is difficult because it is resource and time intensive as it may require duplicative efforts by two pathologists. Some methods for quality assurance include (1) second review of first-time diagnosis cancer cases; (2) periodic reviews of discordant or changed diagnoses by a quality assurance committee; and (3) random review of a subset of cases. These are non-exhaustive, mostly retrospective, and manual. With an automated and systematic QC and QA mechanism, quality can be ensured throughout the workflow for every case. Laboratory quality control and digital pathology quality control are critical to the successful intake, process, diagnosis, and archive of patient specimens. Manual and sampled approaches to QC and QA confer substantial benefits. Systematic QC and QA has the potential to provide efficiencies and improve diagnostic quality.

As described above, computational pathology processes and devices of the present disclosure may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

The digital pathology images described above may be stored with tags and/or labels pertaining to the properties of the specimen or image of the digital pathology image, and such tags/labels may be incorrect or incomplete. Accordingly, the present disclosure is directed to systems and methods for identifying or verifying correct properties (e.g., pertaining to a specimen type) of a digital pathology image. In particular, the disclosed systems and methods may automatically predict the specimen or image properties of a digital pathology image, without relying on the stored tags/labels. Further, the present disclosure is directed to systems and methods for quickly and correctly identifying and/or verifying a specimen type of a digital pathology image, or any information related to a digital pathology image, without necessarily accessing an LIS or analogous information database. One embodiment of the present disclosure may include a system trained to identify various properties of a digital pathology image, based on datasets of prior digital pathology images. The trained system may provide a classification for a specimen shown in a digital pathology image. The classification may help to provide treatment or diagnosis prediction(s) for a patient associated with the specimen.

This disclosure includes one or more embodiments of a specimen classification tool. The input to the tool may include a digital pathology image and any relevant additional inputs. Outputs of the tool may include global and/or local information about the specimen. A specimen may include a biopsy or surgical resection specimen.

Exemplary global outputs of the disclosed tool(s) may contain information about an entire image, e.g., the specimen type, the overall quality of the cut of the specimen, the overall quality of the glass pathology slide itself, and/or tissue morphology characteristics. Exemplary local outputs may indicate information in specific regions of an image, e.g., a particular image region may be classified as having blur or a crack in the slide. The present disclosure includes embodiments for both developing and using the disclosed specimen classification tool(s), as described in further detail below.

FIG. 1A illustrates a block diagram of a system and network for determining specimen property or image property information pertaining to digital pathology image(s), using machine learning, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present application, the electronic network 120 may also be connected to server systems 110, which may include processing devices that are configured to implement a disease detection platform 100, which includes a specimen classification tool 101 for determining specimen property or image property information pertaining to digital pathology image(s), and using machine learning to classify a specimen, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in a LIS 125. However, the correct tissue classification information is not always paired with the image content. Additionally, even if an LIS is used to access the specimen type for a digital pathology image, this label may be incorrect due to the fact that many components of an LIS may be manually inputted, leaving a large margin for error. According to an exemplary embodiment of the present disclosure, a specimen type may be identified without needing to access the LIS 125, or may be identified to possibly correct LIS 125. For example, a third party may be given anonymized access to the image content without the corresponding specimen type label stored in the LIS. Additionally, access to LIS content may be limited due to its sensitive content.

Figure 1B:
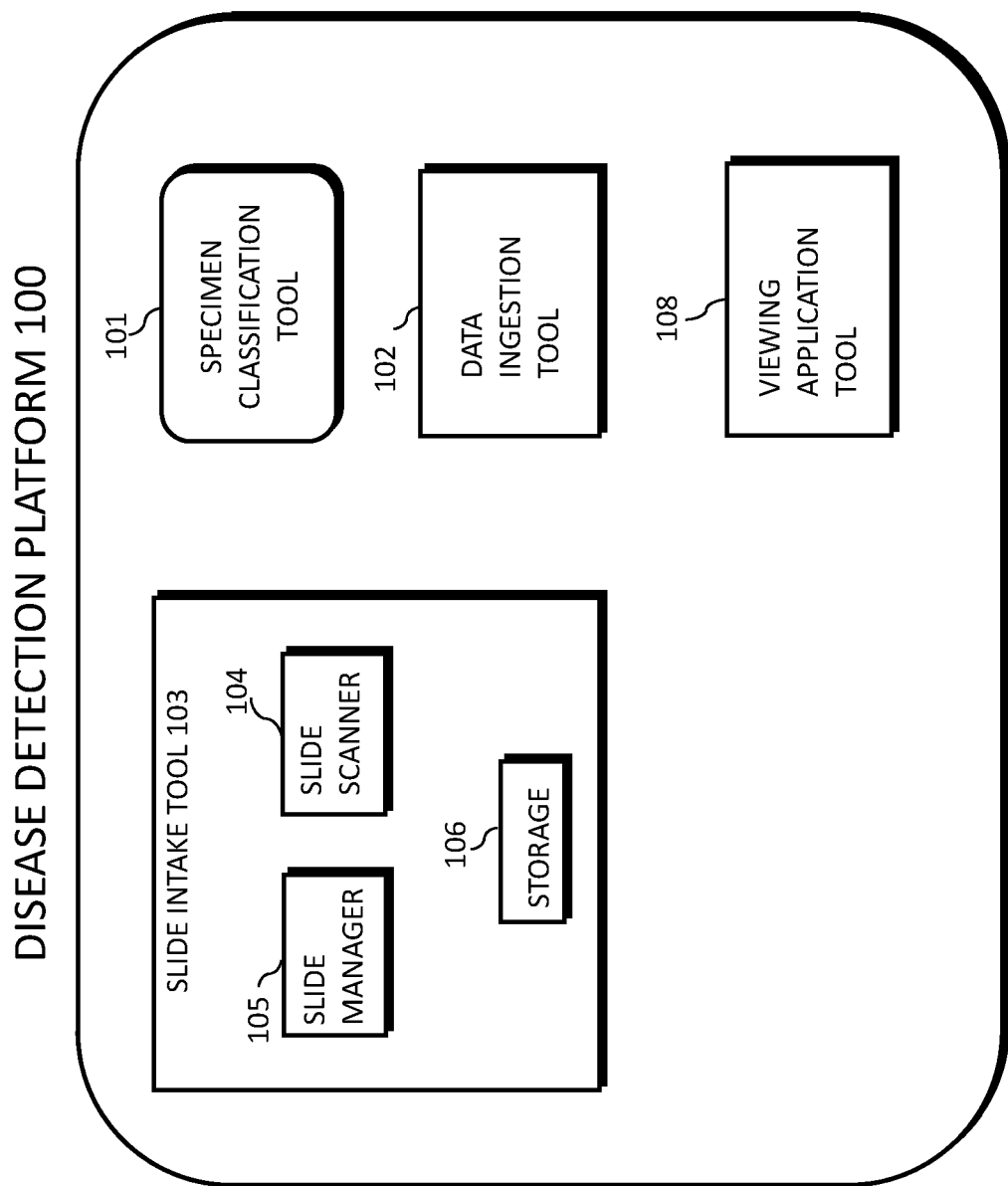
FIG. 1B illustrates an exemplary block diagram of a disease detection platform 100, according to an exemplary embodiment of the present disclosure.

FIG. 1B illustrates an exemplary block diagram of a disease detection platform 100 for determining specimen property or image property information pertaining to digital pathology image(s), using machine learning.

Specifically, FIG. 1B depicts components of the disease detection platform 100, according to one embodiment. For example, the disease detection platform 100 may include a specimen classification tool 101, a data ingestion tool 102, a slide intake tool 103, a slide scanner 104, a slide manager 105, a storage 106, and a viewing application tool 108.

The specimen classification tool 101, as described below, refers to a process and system for determining specimen property or image property information pertaining to digital pathology image(s), and using machine learning to classify a specimen, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., pathologist) with specimen property or image property information pertaining to digital pathology image(s), according to an exemplary embodiment. The information may be provided through various output interfaces (e.g., a screen, a monitor, a storage device, and/or a web browser, etc.).

The specimen classification tool 101, and each of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the specimen classification tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools, and modules may be located on a device that may be connected to an electronic network 120, such as the Internet or a cloud service provider, through one or more computers, servers, and/or handheld mobile devices.

Figure 1C:
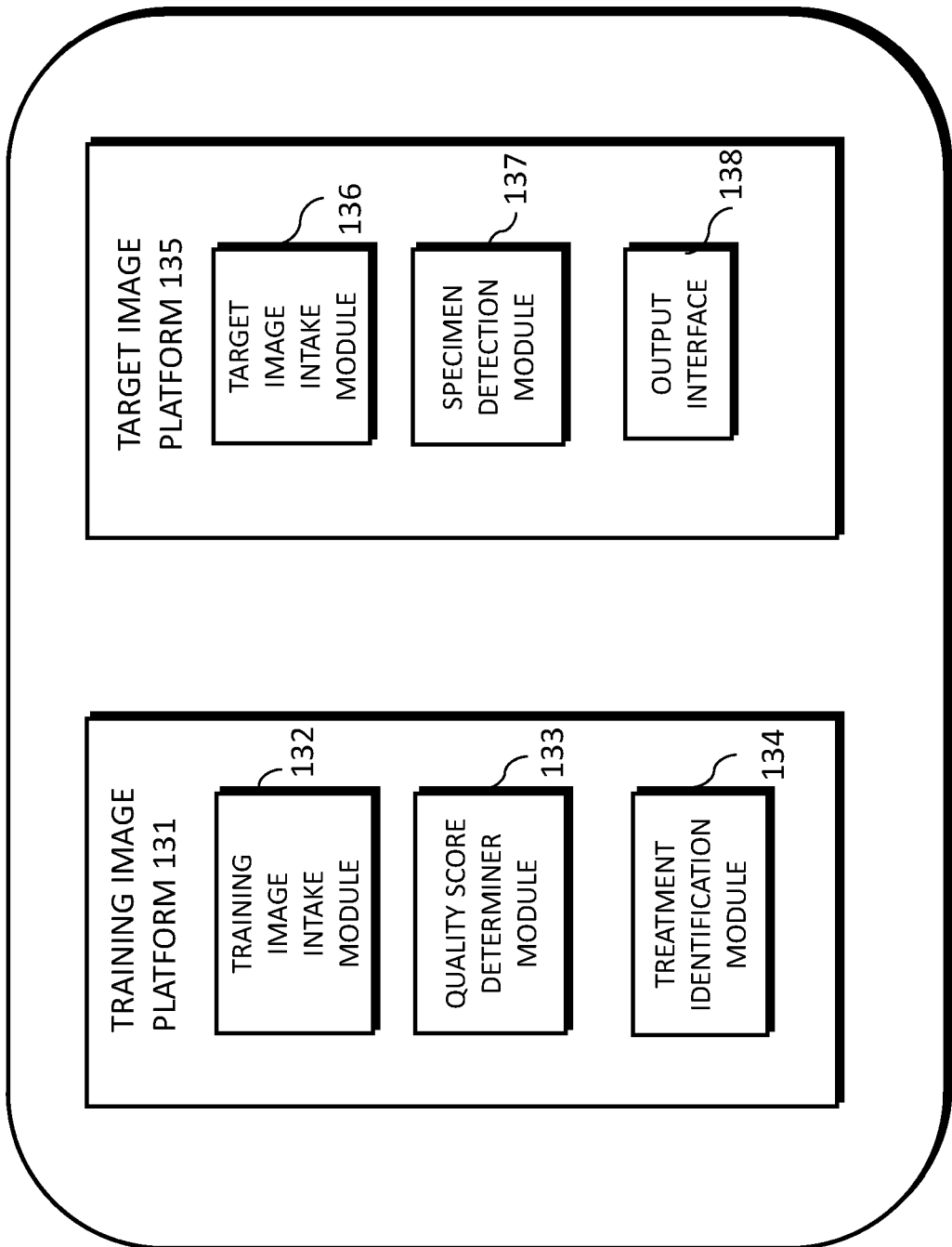
FIG. 1C illustrates an exemplary block diagram of a specimen classification platform, according to an exemplary embodiment of the present disclosure.

FIG. 1C illustrates an exemplary block diagram of a specimen classification tool 101, according to an exemplary embodiment of the present disclosure. The specimen classification tool 101 may include a training image platform 131 and/or a target image platform 135.

According to one embodiment, the training image platform 131 may include a training image intake module 132, a quality score determiner module 133, and/or a treatment identification module 134.

The training image platform 131, according to one embodiment, may create or receive training images that are used to train a machine learning model to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training image intake module 132 may create or receive a dataset comprising one or more training images corresponding to either or both of images of a human tissue and images that are graphically rendered. For example, the training images may be received from any one or any combination of the server systems 110, physician servers 121, hospital servers 122, clinical trial servers 123, research lab servers 124, and/or laboratory information systems 125. This dataset may be kept on a digital storage device. The quality score determiner module 133 may identify quality control (QC) issues (e.g., imperfections) for the training images at a global or local level that may greatly affect the usability of a digital pathology image. For example, the quality score determiner module may use information about an entire image, e.g., the specimen type, the overall quality of the cut of the specimen, the overall quality of the glass pathology slide itself, or tissue morphology characteristics, and determine an overall quality score for the image. The treatment identification module 134 may analyze images of tissues and determine which digital pathology images have treatment effects (e.g., post-treatment) and which images do not have treatment effects (e.g., pre-treatment). It is useful to identify whether a digital pathology image has treatment effects because prior treatment effects in tissue may affect the morphology of the tissue itself. Most LIS do not explicitly keep track of this characteristic, and thus classifying specimen types with prior treatment effects can be desired.

According to one embodiment, the target image platform 135 may include a target image intake module 136, a specimen detection module 137, and an output interface 138. The target image platform 135 may receive a target image and apply the machine learning model to the received target image to determine a characteristic of a target specimen. For example, the target image may be received from any one or any combination of the server systems 110, physician servers 121, hospital servers 122, clinical trial servers 123, research lab servers 124, and/or laboratory information systems 125. The target image intake module 136 may receive a target image corresponding to a target specimen. The specimen detection module 137 may apply the machine learning model to the target image to determine a characteristic of the target specimen. For example, the specimen detection module 137 may detect a specimen type of the target specimen. The specimen detection module 137 may also apply the machine learning model to the target image to determine a quality score for the target image. Further, the specimen detection module 137 may apply the machine learning model to the target specimen to determine whether the target specimen is pre-treatment or post-treatment.

The output interface 138 may be used to output information about the target image and the target specimen. (e.g., to a screen, monitor, storage device, web browser, etc.).

FIG. 2A is a flowchart illustrating an exemplary method of a tool for classifying a specimen, according to an exemplary embodiment of the present disclosure. For example, an exemplary method 200 (e.g., steps 202 to 206) may be performed by the specimen classification tool 101 in response to a request from a user (e.g., physician).

According to one embodiment, the exemplary method 200 for classifying a specimen may include one or more of the following steps. In step 202, the method may include receiving a target image corresponding to a target specimen, the target specimen comprising a tissue sample of a patient. For example, the target image may be received from any one or any combination of the server systems 110, physician servers 121, hospital servers 122, clinical trial servers 123, research lab servers 124, and/or laboratory information systems 125.

In step 204, the method may include applying a machine learning model to the target image to determine at least one characteristic of the target specimen and/or at least one characteristic of the target image. Determining the characteristic of the target specimen may include determining a specimen type of the target specimen. Further, according to one embodiment, determining the characteristic of the target specimen may include identifying a confidence value corresponding to the specimen type of the target specimen. For example, the machine learning model may indicate a level of confidence in the specimen type, according to various parameters. This may be done by using a range of means, including, but not limited to, using a neural network to compute a probability score for one or more characteristics and thresholding that probability. An alternative to this approach is to examine the entropy of the outputs produced by a probabilistic machine learning system, where high entropy indicates greater uncertainty. Additionally, determining the characteristic of the target image may include identifying a quality score for each of the training images. For example, the method may include applying the trained machine learning model predicting a presence of quality control (QC) issues. For example, the method may include identifying quality control issues (e.g., poorly cut specimen sections, scanning artifacts, damaged slides, markings on slides, etc.), and/or recommending an action (e.g., rescan of image, recut, slide reconstruction, etc.) to mitigate the issue. According to one embodiment, the determining the characteristic of the target image may include identifying an amount of treatment effects in a target image and outputting a predicted degree to which a tissue of the target image has been treated.

The machine learning model may have been generated by processing a plurality of training images to predict at least one characteristic, and the training images may include images of human tissue and/or images that are algorithmically generated. The machine learning model may be implemented using machine learning methods for classification and regression. Training inputs could include real or synthetic imagery. Training inputs may or may not be augmented (e.g., adding noise or creating variants of the input by flipping/distortions). Exemplary machine learning models may include, but are not limited to, any one or any combination of Neural Networks, Convolutional neural networks, Random Forest, Logistic Regression, and Nearest Neighbor. Convolutional neural networks can directly learn the image feature representations necessary for discriminating among characteristics, which can work extremely well when there are large amounts of data to train on for each specimen, whereas the other methods can be used with either traditional computer vision features, e.g., SURF or SIFT, or with learned embeddings (e.g., descriptors) produced by a trained convolutional neural network, which can yield advantages when there are only small amounts of data to train on. The training images may be received from any one or any combination of the server systems 110, physician servers 121, hospital servers 122, clinical trial servers 123, research lab servers 124, and/or laboratory information systems 125. This dataset may be kept on a digital storage device. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, IHC, molecular pathology, etc.; and/or (b) digitized tissue samples from a 3D imaging device, such as microCT.

In step 206, the method may include outputting the at least one characteristic of the target specimen and/or the at least one characteristic of the target image. If unable to determine a specimen type, the method may include outputting an alert indicating that the specimen type of the target specimen is not identifiable.

Figure 2B:
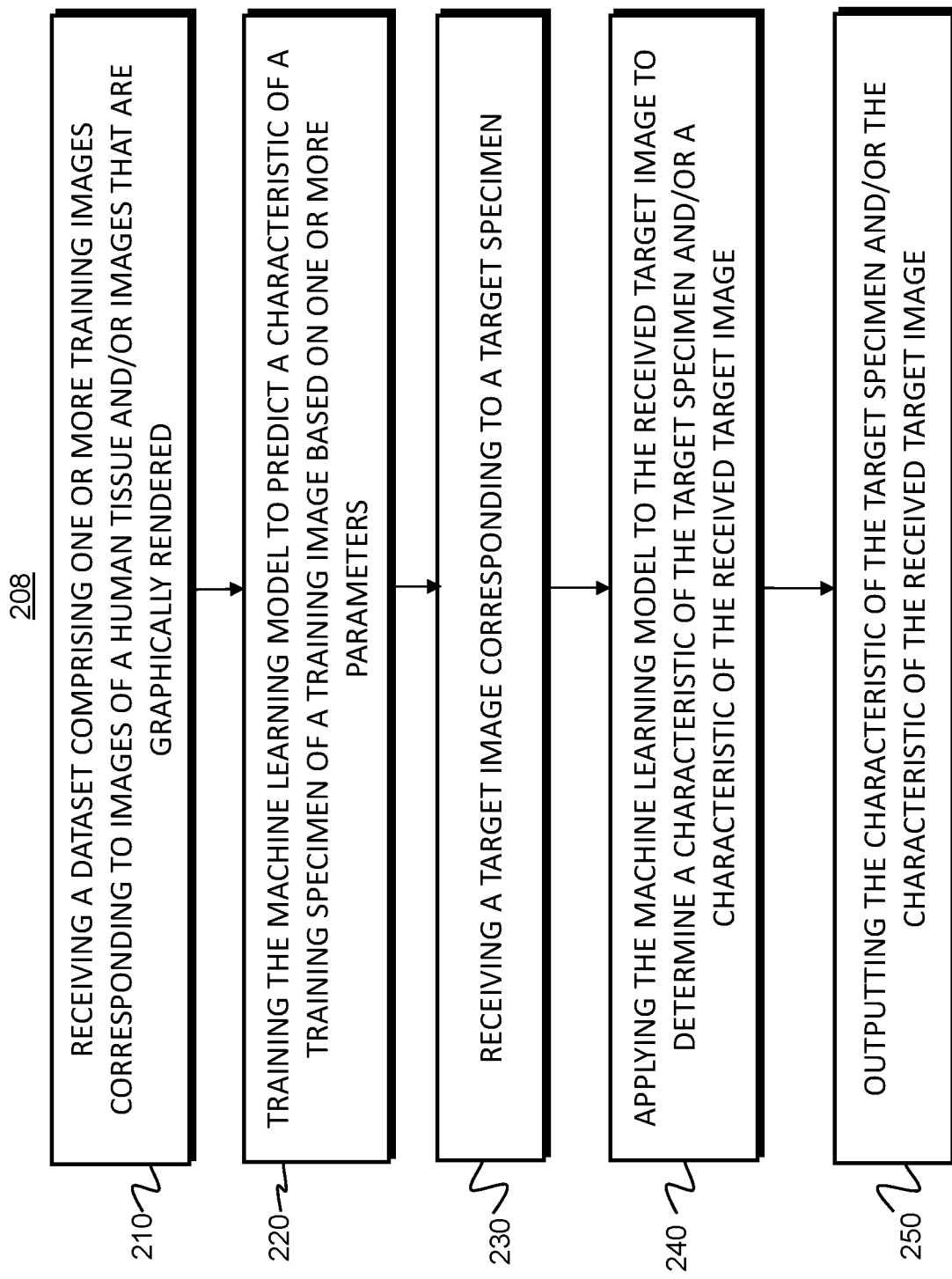

FIG. 2B is a flowchart illustrating an exemplary method of a tool for classifying a specimen, according to an exemplary embodiment of the present disclosure. For example, an exemplary method 208 (e.g., steps 210 to 250) may be performed by the specimen classification tool 101 in response to a request from a user (e.g., physician).

According to one embodiment, the exemplary method 208 for classifying a specimen may include one or more of the following steps. In step 210, a machine learning model may create or receive a dataset comprising one or more training images corresponding to either or both of images of a human tissue and images that are graphically rendered. For example, the training images may be received from any one or any combination of the server systems 110, physician servers 121, hospital servers 122, clinical trial servers 123, research lab servers 124, and/or laboratory information systems 125. This dataset may be kept on a digital storage device. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, IHC, molecular pathology, etc.; and/or (b) digitized tissue samples from a 3D imaging device, such as microCT.

In step 220, a machine learning model may be trained to predict a characteristic of a training specimen of a training image based on one or more parameters. For example, a machine learning model may have its parameters fit (e.g., a neural network trained with backpropagation) to predict the labels in the training set, which may allow the model to replicate the correct output behavior (e.g., corresponding labels) when given a digital pathology image as input. This machine learning model may be implemented using machine learning methods for classification and regression. Training inputs could include real or synthetic imagery. Training inputs may or may not be augmented (e.g., adding noise). Exemplary machine learning models may include, but are not limited to, any one or any combination of Neural Networks, Convolutional neural networks, Random Forest, Logistic Regression, and Nearest Neighbor.

In step 230, the method may include receiving a digital pathology image (e.g., target image). For example, the target image may be received from any one or any combination of the server systems 110, physician servers 121, hospital servers 122, clinical trial servers 123, research lab servers 124, and/or laboratory information systems 125. In step 240, the method may include applying the machine learning model to the received target image to determine a characteristic of the target specimen. Determining the characteristic of the target specimen may include determining a specimen type of the target specimen. Further, according to one embodiment, determining the characteristic of the target specimen may include identifying a confidence value corresponding to the specimen type of the target specimen. For example, the machine learning model may indicate a level of confidence in the specimen type, according to various parameters. Additionally, determining the characteristic of the target image may include identifying a quality score for each of the training images. For example, the method may include applying the trained machine learning model predicting a presence of quality control (QC) issues. The method may include identifying quality control issues (e.g., poorly cut specimen sections, scanning artifacts, damaged slides, markings on slides, etc.), and/or recommending an action (e.g., rescan of image, recut, slide reconstruction, etc.) to mitigate the issue. According to one embodiment, the determining the characteristic of the target image may include identifying an amount of treatment effects in a target image and outputting a predicted degree to which a tissue of the target image has been treated.

In step 250, the method may include outputting a characteristic of the target specimen to a monitor, digital storage device, etc. If unable to determine a specimen type, the method may include outputting an alert indicating that the specimen type of the target specimen is not identifiable.

Figure 3:
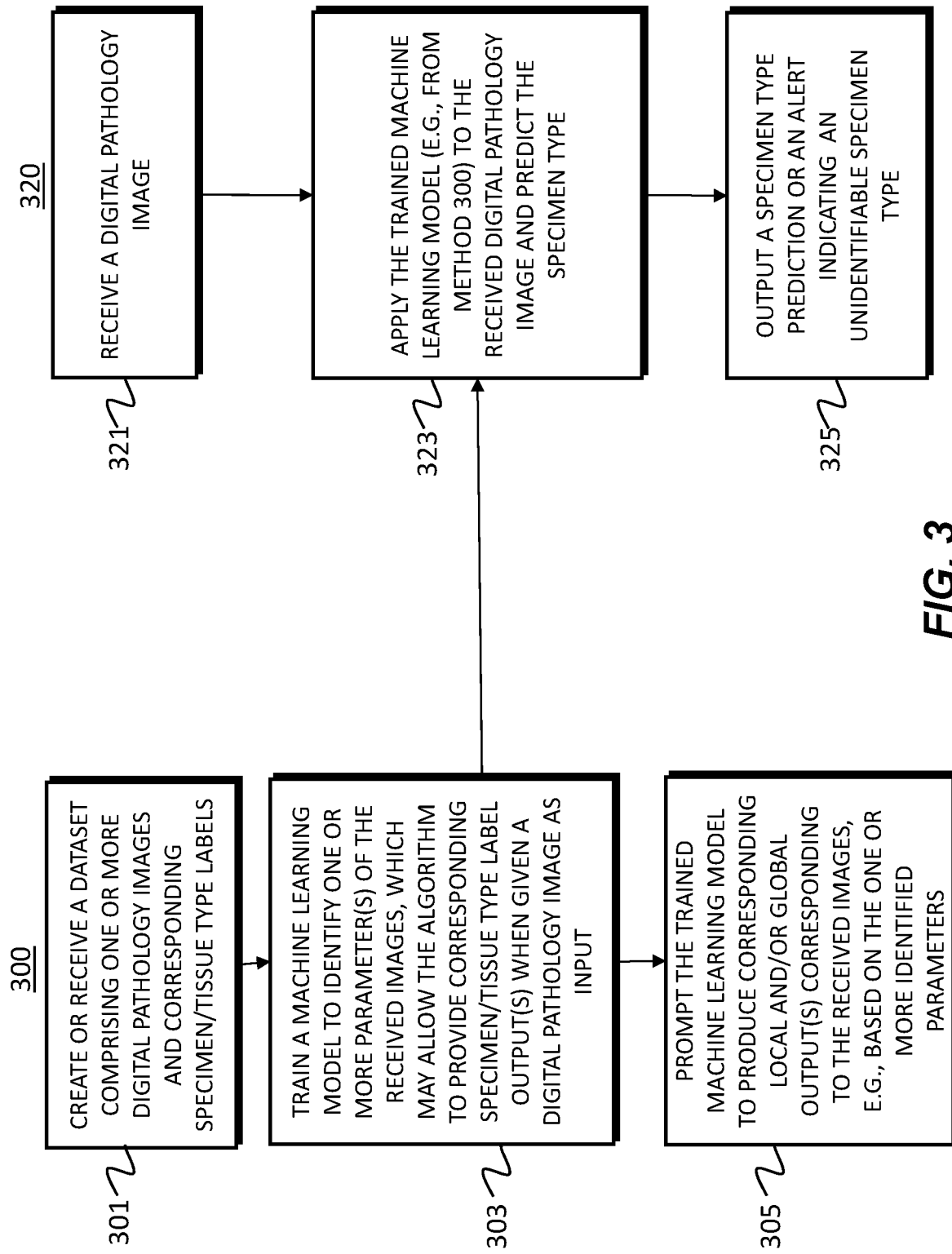
FIG. 3 is a flowchart of an exemplary embodiment of determining specimen property or image property information pertaining to digital pathology image(s), according to an exemplary embodiment of the present disclosure.

FIG. 3 illustrates exemplary methods of a tool for determining specimen property or image property information pertaining to digital pathology image(s), using machine learning. For example, exemplary methods 300 and 320 (e.g., steps 301-325) may be performed by the specimen classification tool 101 in response to a request from a user (e.g., physician).

According to one embodiment, the exemplary method 300 for developing the specimen classification tool 101 may include one or more of the following steps. In step 301, a machine learning model may create or receive a dataset comprising one or more digital pathology images and corresponding specimen/tissue type labels. For example, the images may be received from any one or any combination of the server systems 110, physician servers 121, hospital servers 122, clinical trial servers 123, research lab servers 124, and/or laboratory information systems 125. This dataset may be kept on a digital storage device. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, IHC, molecular pathology, etc.; and/or (b) digitized tissue samples from a 3D imaging device, such as microCT.

In step 303, a machine learning model may train a parametric or non-parametric machine learning model, e.g., in which a machine learning model may identify parameters of the images and corresponding labels in the dataset, which may allow the model to replicate the correct output behavior (e.g., corresponding labels) when given a digital pathology image as input. This machine learning model may be implemented using machine learning methods for classification and regression. Training inputs could include real or synthetic imagery. Training inputs may or may not be augmented (e.g., adding noise). Exemplary machine learning models may include, but are not limited to any one or any combination of Neural Networks, Convolutional neural networks, Random Forest, Logistic Regression, and Nearest Neighbor.

In step 305, a machine learning model may be prompted to produce local and global output(s) for the pathology images, e.g., based on the one or more identified parameters of the machine learning model. Such output(s) may be to a monitor, a digital storage device, etc.

According to one embodiment, an exemplary method 320 for using the specimen classification tool 101 may include one or more of the steps below. In step 321, the method may include receiving a digital pathology image from a user. For example, the image may be received from any one or any combination of the server systems 110, physician servers 121, hospital servers 122, clinical trial servers 123, research lab servers 124, and/or laboratory information systems 125. In step 323, the method may include applying the trained system to the digital pathology image and predict the specimen type. In step 325, the method may include outputting a specimen type prediction to a monitor, digital storage device, etc.

Further, in step 325, the method may include comparing the predicted specimen information to the information provided in an LIS or elsewhere. If the predicted information does not match the stored information, or is not within a predetermined margin of the stored information, an alert may be generated or a system may alter its processing behavior of the input and/or correct the stored information due to this mismatch. The method may include using the predicted specimen type to initiate another machine learning model or machine learning model for processing a received image or related information from a user (e.g., a tissue donor). Examples may include a diagnostic model to perform an automated diagnosis from this specific specimen type or providing contextual information to a system capable of processing images from many kinds of tissues. If the specimen type cannot be identified, the method may include generating an alert to the system or user.

The above-described specimen classification tool 101 may include particular applications or embodiments usable in research, and/or production/clinical/industrial settings. These are described in detail below.

An exemplary method of identifying specimen types may be used for many applications of digital pathology. For example, identifying specimen types may be desired for institutions that receive access to digital pathology images, where the image information or access to the image information lacks corresponding specimen type information (e.g., from an LIS). Identification may also be desired for internal hospital usage if digital pathology images need to be sent to specimen-specific diagnosis or diagnosis-aide tools. Identification may be used as a form of verification to ensure that an LIS-provided specimen type label is indeed correct.

Figure 4:
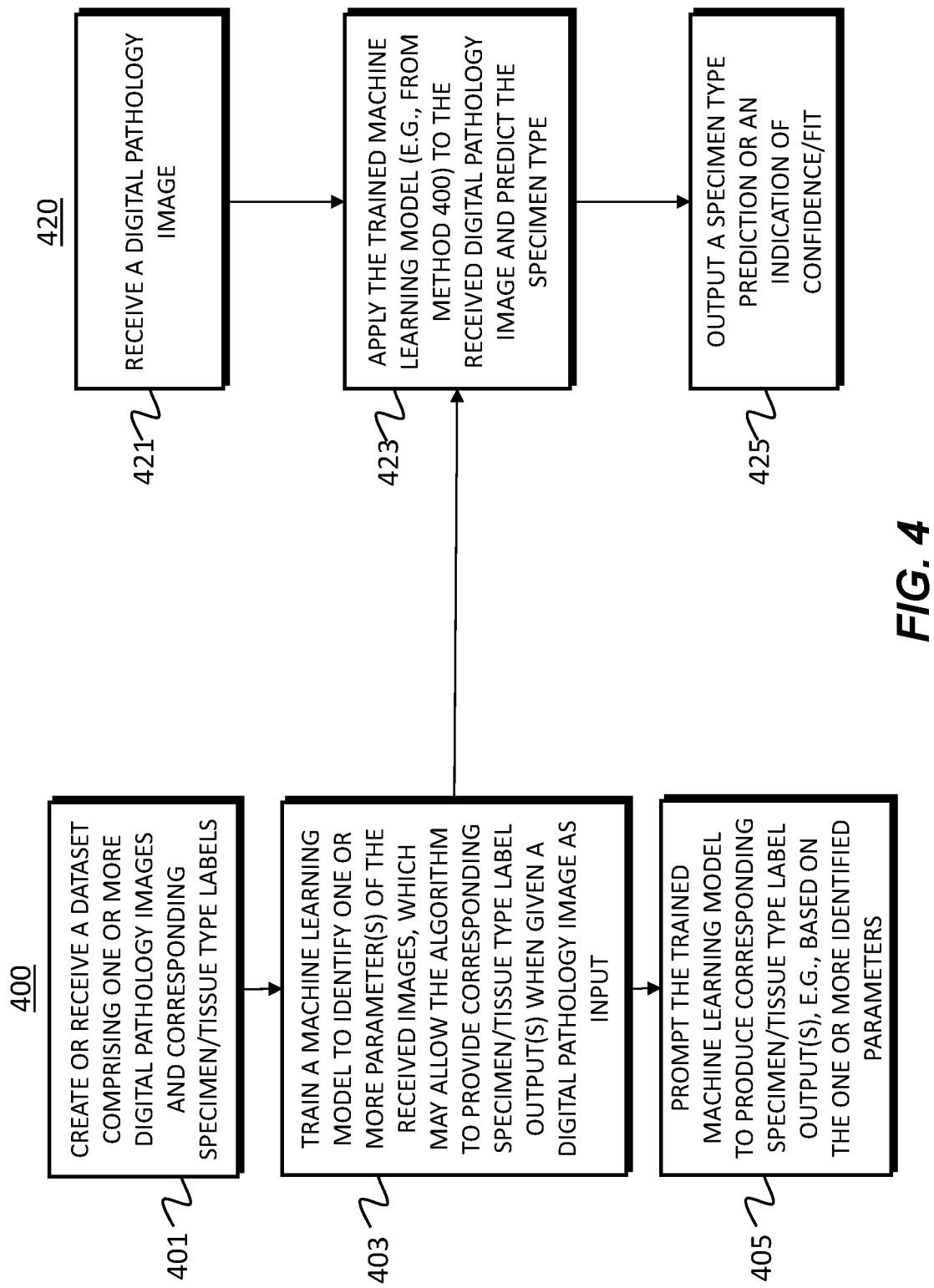
FIG. 4 is a flowchart of an exemplary embodiment of generating and using a specimen type identification tool, according to an exemplary embodiment of the present disclosure.

FIG. 4 illustrates an exemplary method for a specimen type identification tool. For example, an exemplary method 400 may be performed by the specimen classification tool 101 in response to a request from a user (e.g., physician). According to one embodiment, the exemplary method 400 for developing a specimen type identification tool may include one or more of the steps below. In step 401, a machine learning model may create or receive a dataset of digital pathology images and their corresponding specimen type label. For example, the images may be received from any one or any combination of the server systems 110, physician servers 121, hospital servers 122, clinical trial servers 123, research lab servers 124, and/or laboratory information systems 125. This dataset may include one or more specimen types that the model is intended to classify. This step may also include determining the one or more specimen types that the model is intended to classify. This dataset may be kept on a digital storage device. Datasets with one specimen type may be used to verify LIS-given specimen type labels. Datasets with many specimen types may be used for broader identification purposes.

In step 403, a machine learning model may train a machine learning model to classify each digital pathology image according to its specimen type. This model may take the digital pathology images and corresponding specimen type labels as inputs. This model may be implemented using any machine learning classification model. Examples of implementations may include, but are not limited to any one or any combination of Neural Networks, Random Forest, Logistic Regression, Nearest Neighbor, and Density estimation approaches. Convolutional neural networks may directly learn the image feature representations used for discriminating the specimen type, which may work well if there are large amounts of data to train on for each specimen, whereas the other methods may be used with either traditional computer vision features, e.g., SURF or SIFT, or with learned embeddings (e.g., descriptors) produced by a trained convolutional neural network, which may yield advantages if there are smaller amounts of data to train on. In step 405, a machine learning model may be prompted to output labels for an individual pathology image to a digital storage device.

According to one embodiment, an exemplary method 420 for using the specimen type identification tool may include one or more of the steps below. In step 421, the method may include receiving a digital pathology image. For example, the image may be received from any one or any combination of the server systems 110, physician servers 121, hospital servers 122, clinical trial servers 123, research lab servers 124, and/or laboratory information systems 125. In step 423, the method may include applying the trained machine learning model of the exemplary specification type tool to the received digital pathology image and predict the specimen type. In step 425, the method may include outputting a specimen type prediction for an image label, e.g., to a screen, monitor, storage device, etc. If the machine learning model is being used to verify an existing specimen type label for a digital pathology image, the machine learning model may output an indication of confidence or fit for the given label to a screen, monitor, storage device, etc.

Figure 5:
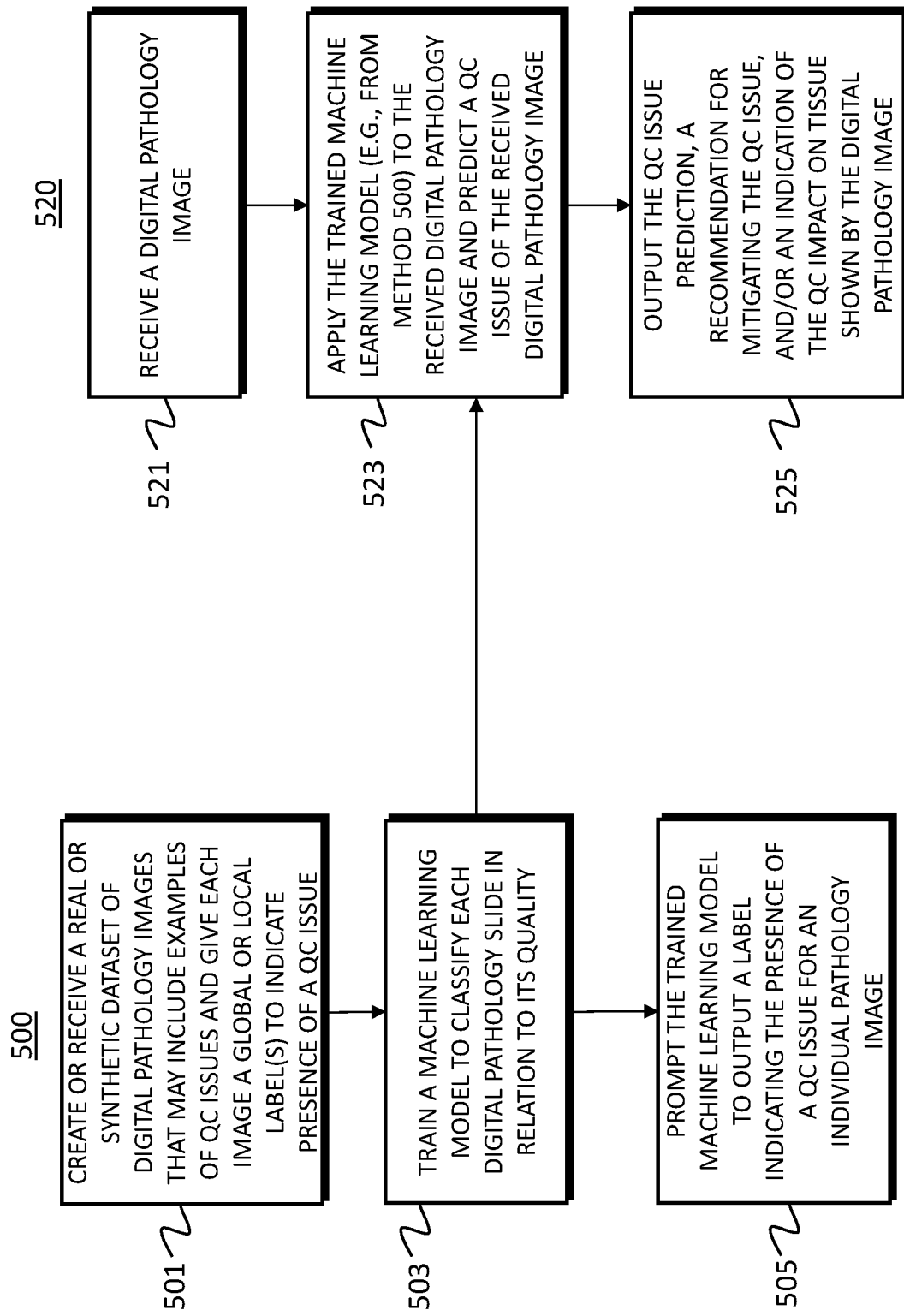
FIG. 5 is a flowchart of an exemplary embodiment of generating and using an image quality control and/or specimen quality control tool, according to an exemplary embodiment of the present disclosure.

FIG. 5 illustrates an exemplary embodiment of a specimen classification tool 101 that may be used to identify quality control (QC) issues (e.g., imperfections) at a global or local level that may greatly affect the usability of a digital pathology image. For example, exemplary methods 500 and 520 (e.g., steps 501-525) may be performed by the specimen classification tool 101 in response to a request from a user (e.g., physician). The exemplary method 500 may be useful given that QC related information for digital pathology images may not be stored in an LIS or any digital storage device.

According to one embodiment, the exemplary method 500 for developing a quality control tool may include one or more of the steps below. In step 501, a machine learning model may create or receive a real or synthetic dataset of digital pathology images that may include examples of QC issues and give each image a global or local label(s) to indicate presence of a QC issue. For example, the images may be received from any one or any combination of the server systems 110, physician servers 121, hospital servers 122, clinical trial servers 123, research lab servers 124, and/or laboratory information systems 125. This dataset may be kept on a digital storage device. QC labels may include but are not limited to: poorly cut specimen sections, scanning artifacts, damaged slides, markings on slides, etc.

In step 503, a machine learning model may train a machine learning model to classify each digital pathology slide in relation to its quality. This model may take the digitized pathology images and corresponding QC labels as input. Exemplary machine learning models may include, but are not limited to any one or any combination of Neural Networks, Random Forest, Logistic Regression, and Nearest Neighbor. In step 505, a machine learning model may be prompted to output a label indicating the presence of a QC issue for an individual pathology image to a digital storage device.

According to one embodiment, an exemplary method 520 for using a QC tool may include one or more of the steps below. In step 521, the method may include obtaining or receiving a digital pathology image. For example, the image may be received from any one or any combination of the server systems 110, physician servers 121, hospital servers 122, clinical trial servers 123, research lab servers 124, and/or laboratory information systems 125. In step 523, the method may include applying the trained machine learning model of the QC tool and predict presence of QC issues. In step 525, the method may include outputting a prediction to a digital storage device, e.g., to a screen, monitor, storage device, etc. The method may include outputting the type of QC issue (poorly cut specimen, scanning artifacts, etc.), and/or recommending an action (rescan of image, recut, etc.) to mitigate the issue, e.g., to a screen, monitor, storage device, etc. The method may include outputting whether the QC issue on the image directly affects the tissue itself. This may be useful for understanding if the digital image is still useable by a pathologist, e.g., to a screen, monitor, storage device, etc.

Figure 6:
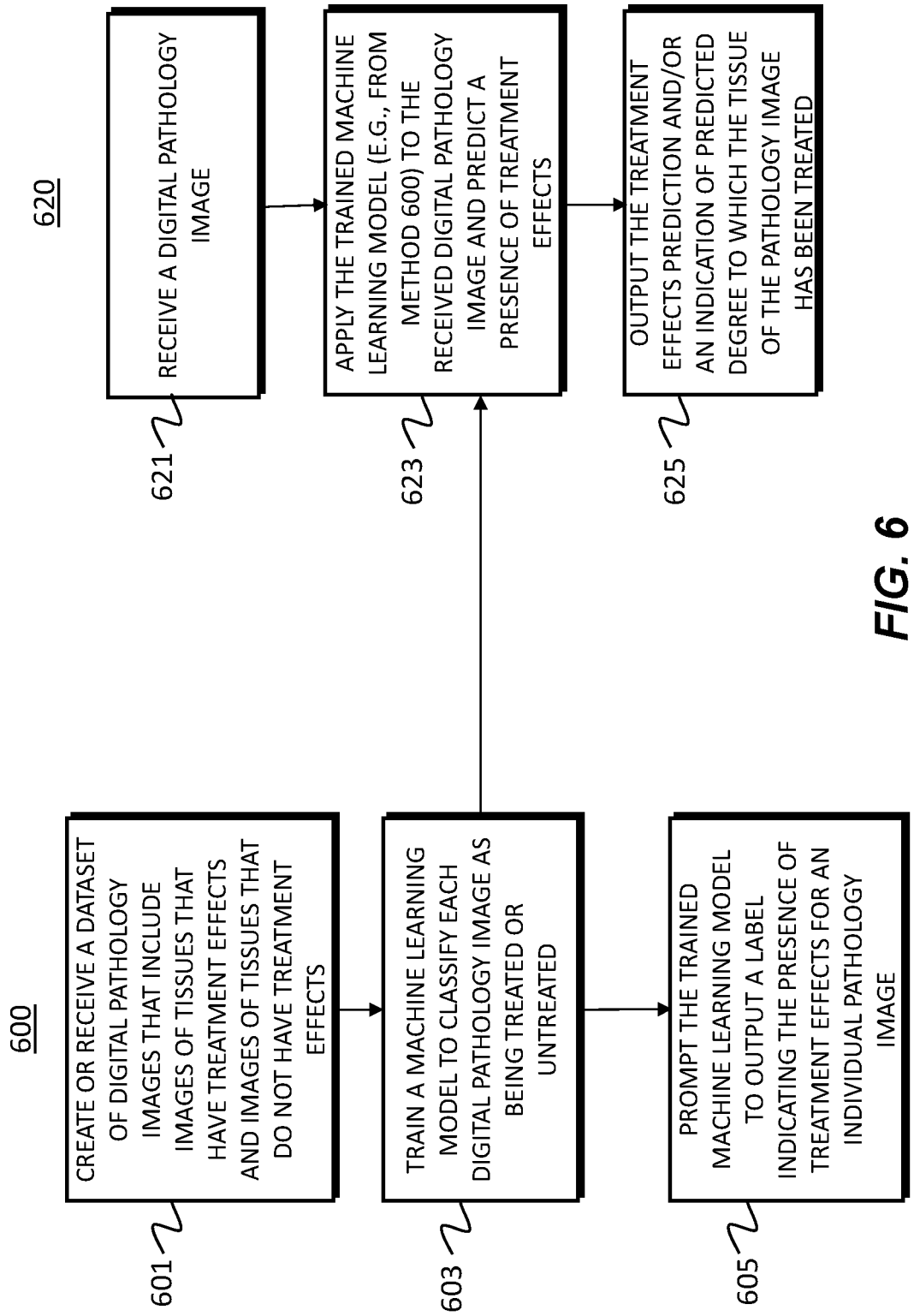
FIG. 6 is a flowchart of an exemplary embodiment of generating and using a prior tissue treatment effect identification tool, according to an exemplary embodiment of the present disclosure.

FIG. 6 illustrates an exemplary embodiment of generating and using a prior tissue treatment effect identification tool, according to an exemplary embodiment of the present disclosure. Prior treatment effects in tissue may affect the morphology of the tissue itself. Most LIS do not explicitly keep track of this characteristic, and thus classifying specimen types with prior treatment effects can be desired. A system for detecting treatment effects in one or more tissue types is described below. For example, exemplary methods 600 and 620 (e.g., steps 601-625) may be performed by the specimen classification tool 101 in response to a request from a user (e.g., physician).

According to one embodiment, the exemplary method 600 for developing a prior tissue treatment effect identification tool may include one or more of the steps below. In step 601, a machine learning model may create or receive a dataset of digital pathology images that include images of tissues that have treatment effects and images of tissues that do not have treatment effects. For example, the images may be received from any one or any combination of the server systems 110, physician servers 121, hospital servers 122, clinical trial servers 123, research lab servers 124, and/or laboratory information systems 125. This dataset may either contain images for a single tissue type or multiple tissue types. This dataset may be kept on a digital storage device.

In step 603, a machine learning model may train a machine learning model to classify each digital pathology image as being treated (e.g., post-treatment) or untreated (pre-treatment). If the patient has treatment effects, the model may also be trained on the degree of treatment effects. This model may take the digitized pathology images and corresponding treatment effect labels as input. This model may be trained using supervised learning classification methods or unsupervised density estimation or anomaly detection methods. Examples of supervised learning implementations may include any one or any combination of Neural Networks, Random Forest, Logistic Regression, and Nearest Neighbor. In step 605, a machine learning model may be prompted to output a label indicating a presence of treatment effects for an individual pathology image to a digital storage device (e.g., post-treatment).

According to one embodiment, an exemplary method 620 for using the prior tissue treatment effect identification tool may include one or more of the steps below. In step 621, the method may include obtaining or receiving a digital pathology image. For example, the image may be received from any one or any combination of the server systems 110, physician servers 121, hospital servers 122, clinical trial servers 123, research lab servers 124, and/or laboratory information systems 125. In step 623, the method may include applying the trained machine learning model of the exemplary prior treatment effect tool and predict a presence of treatment effects. In step 625, the method may include outputting the prediction, e.g., to a screen, monitor, storage device, etc. The method may include outputting an indication of a degree to which the tissue of the pathology image has been treated, e.g., to a screen, monitor, storage device, etc.

Figure 7:
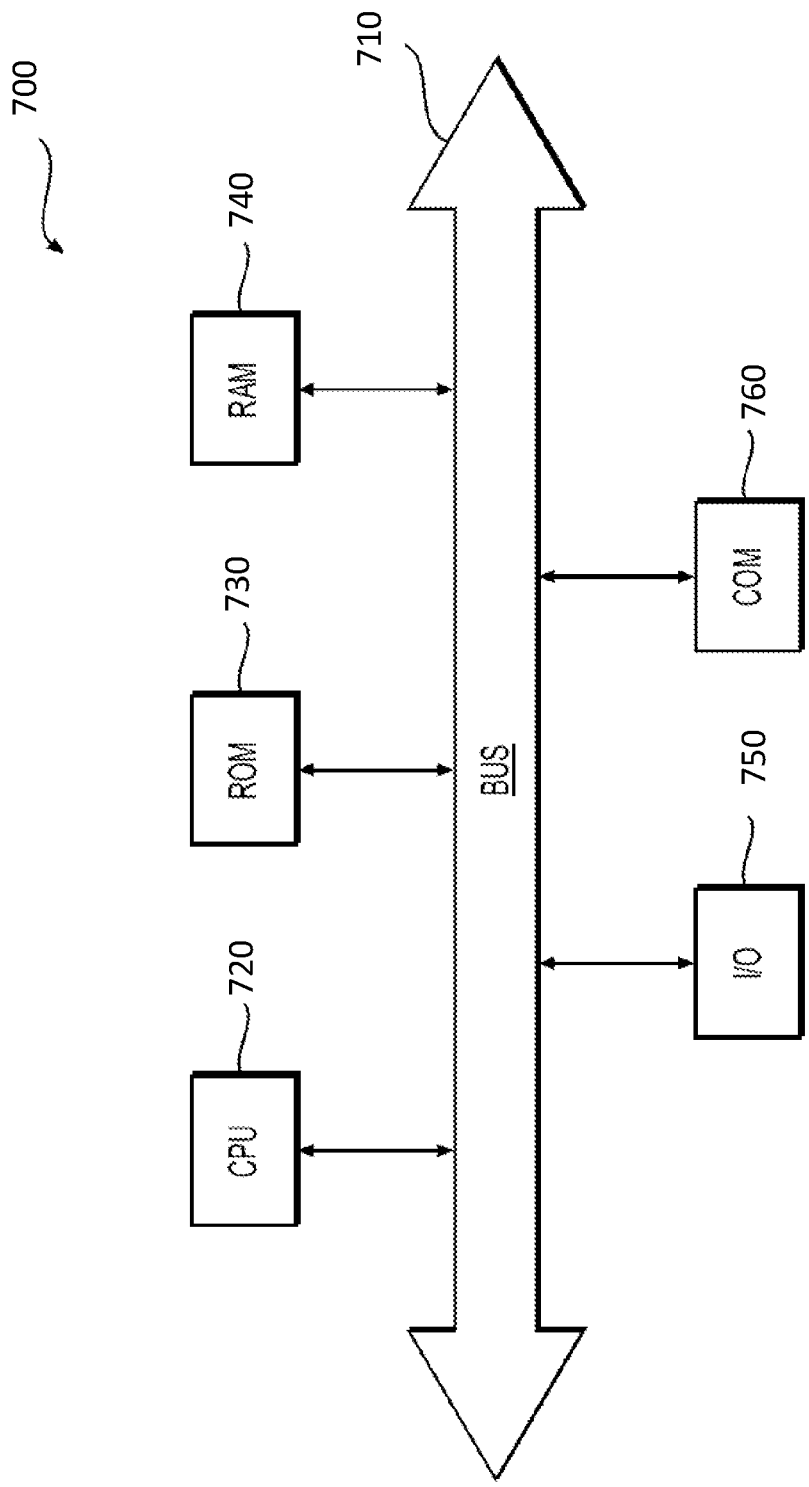
FIG. 7 depicts an example system that may execute techniques presented herein.

As shown in FIG. 7, device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multi-processor system, such system operating alone, or in a cluster of computing devices operating in a cluster or server farm. CPU 720 may be connected to a data communication infrastructure 710, for example, a bus, message queue, network, or multi-core message-passing scheme.

Device 700 also may include a main memory 740, for example, random access memory (RAM), and also may include a secondary memory 730. Secondary memory 730, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include other similar means for allowing computer programs or other instructions to be loaded into device 700. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical, or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 700 also may include input and output ports 750 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:

1. A computer-implemented method for analyzing an image corresponding to a specimen, the method comprising:
   receiving a target image corresponding to a target specimen, the target specimen comprising a tissue sample of a patient;
   applying a machine learning system to the target image to determine at least one characteristic of the target specimen and/or at least one characteristic of the target image, the machine learning system having been generated by processing a plurality of training images to identify a quality assessment and predict at least one characteristic, the quality assessment being based on a specimen cut, a scanning parameter, a slide reconstruction, and/or a slide marking, the training images comprising images of human tissue and/or images that are algorithmically generated; and
   outputting the at least one characteristic of the target specimen and/or the at least one characteristic of the target image.

2. The computer-implemented method of claim 1, further comprising:
   determining a prediction of a specimen type of the target specimen based on the at least one characteristic of the target specimen; and
   outputting the prediction of the specimen type of the target specimen.

3. The computer-implemented method of claim 1, further comprising:
   determining a prediction of a specimen type of the target specimen based on the at least one characteristic of the target specimen;
   determining whether a confidence value of the prediction exceeds a predetermined threshold; and
   in response to determining that the confidence value of the prediction does not exceed the predetermined threshold, outputting an alert indicating that the specimen type of the target specimen is not identifiable.

4. The computer-implemented method of claim 1, further comprising:
   determining a confidence value of a prediction of a specimen type of the target specimen based on the at least one characteristic of the target specimen; and
   outputting the confidence value.

5. The computer-implemented method of claim 4, further comprising:
   identifying a prior treatment associated with the patient; and
   determining the confidence value of the prediction of the specimen type based at least in part on the prior treatment associated with the patient.

6. The computer-implemented method of claim 1, further comprising:
   determining whether the quality assessment for the target image is less than a predetermined value; and
   in response to the quality assessment for the target image being less than the predetermined value, outputting a recommendation for increasing a quality of the target image.

7. The computer-implemented method of claim 6, wherein the recommendation comprises a specimen cut, a scanning parameter, a slide reconstruction, and/or a slide marking.

8. The computer-implemented method of claim 1, further comprising:
   determining, using the target image and the machine learning system, whether the target specimen is post-treatment or pre-treatment.

9. The computer-implemented method of claim 1, further comprising:
   determining, using the target image and the machine learning system, whether the target specimen is post-treatment or pre-treatment;
   upon determining that the target specimen is post-treatment, determining a predicted degree to which the target specimen has been treated based on the target image; and outputting the predicted degree to which the target specimen has been treated.

10. A system for analyzing an image corresponding to a specimen, the system comprising:
at least one memory storing instructions; and
at least one processor executing the instructions to perform operations comprising:
receiving a target image corresponding to a target specimen, the target specimen comprising a tissue sample of a patient;
applying a machine learning system to the target image to determine at least one characteristic of the target specimen and/or at least one characteristic of the target image, the machine learning system having been generated by processing a plurality of training images to identify a quality assessment and predict at least one characteristic, the quality assessment being based on any one or any combination of a specimen cut, a scanning parameter, a slide reconstruction, and/or a slide marking, the training images comprising images of human tissue and/or images that are algorithmically generated; and
outputting the at least one characteristic of the target specimen and/or the at least one characteristic of the target image.

11. The system of claim 10, the operations further comprising:
determining a prediction of a specimen type of the target specimen based on the at least one characteristic of the target specimen; and
outputting the prediction of the specimen type of the target specimen.

12. The system of claim 10, the operations further comprising:
determining a prediction of a specimen type of the target specimen based on the at least one characteristic of the target specimen;
determining whether a confidence value of the prediction exceeds a predetermined threshold; and
in response to determining that the confidence value of the prediction does not exceed the predetermined threshold, outputting an alert indicating that the specimen type of the target specimen is not identifiable.

13. The system of claim 10, the operations further comprising:
determining a confidence value of a prediction of a specimen type of the target specimen based on the at least one characteristic of the target specimen; and
outputting the confidence value.

14. The system of claim 13, the operations further comprising:
identifying a prior treatment associated with the patient; and
determining the confidence value of the prediction of the specimen type based at least in part on the prior treatment associated with the patient.

15. The system of claim 10, the operations further comprising:
determining whether the quality assessment for the target image is less than a predetermined value; and
in response to the quality assessment for the target image being less than the predetermined value, outputting a recommendation for increasing a quality of the target image.

16. The system of claim 15, wherein the recommendation comprises a specimen cut, a scanning parameter, a slide reconstruction, and/or a slide marking.

17. The system of claim 10, the operations further comprising:
determining, using the target image and the machine learning system, whether the target specimen is post-treatment or pre-treatment.

18. The system of claim 10, the operations further comprising:
determining, using the target image and the machine learning system, whether the target specimen is post-treatment or pre-treatment;
upon determining that the target specimen is post-treatment, determining a predicted degree to which the target specimen has been treated based on the target image; and
outputting the predicted degree to which the target specimen has been treated.

19. A non-transitory computer-readable medium storing instructions that, when executed by processor, cause the processor to perform a method for analyzing an image corresponding to a specimen, the method comprising:
receiving a target image corresponding to a target specimen, the target specimen comprising a tissue sample of a patient;
applying a machine learning system to the target image to determine at least one characteristic of the target specimen and/or at least one characteristic of the target image, the machine learning system having been generated by processing a plurality of training images to identify a quality assessment and predict at least one characteristic, the quality assessment being based on a specimen cut, a scanning parameter, a slide reconstruction, and/or a slide marking, the training images comprising images of human tissue and/or images that are algorithmically generated; and
outputting the at least one characteristic of the target specimen and/or the at least one characteristic of the target image.

20. The non-transitory computer-readable medium of claim 19, further comprising:
determining a prediction of a specimen type of the target specimen based on the at least one characteristic of the target specimen; and
outputting the prediction of the specimen type of the target specimen.

* * * * *